United States Patent [19]
Chowhan et al.

[11] Patent Number: 5,948,738
[45] Date of Patent: *Sep. 7, 1999

[54] STABLE LIQUID ENZYME COMPOSITIONS AND METHODS OF USE IN CONTACT LENS CLEANING AND DISINFECTING SYSTEMS

[75] Inventors: Masood A. Chowhan; Ronald P. Quintana; Bahram Asgharian; Bor-Shyue Hong, all of Arlington, Tex.; Thierry Bilbault, Morris Township, N.J.; Ruth A. Rosenthal, Alvarado, Tex.

[73] Assignee: Alcon Laboratories, Inc., Fort Worth, Tex.

[ * ] Notice: This patent is subject to a terminal disclaimer.

[21] Appl. No.: 09/167,031

[22] Filed: Oct. 6, 1998

Related U.S. Application Data

[63] Continuation of application No. 08/687,334, Aug. 2, 1996, which is a continuation-in-part of application No. 08/544,753, Oct. 18, 1995, Pat. No. 5,723,421, which is a continuation-in-part of application No. 08/477,001, Jun. 7, 1995, Pat. No. 5,604,190.

[51] Int. Cl.$^6$ .............................. C11D 3/04; C11D 3/18; C11D 3/37; C11D 3/382
[52] U.S. Cl. .......................... 510/114; 510/392; 510/393; 510/420; 510/530
[58] Field of Search .................................. 510/114, 392, 510/393, 420, 530

[56] References Cited

U.S. PATENT DOCUMENTS

| | | |
|---|---|---|
| Re. 32,672 | 5/1988 | Huth et al. ............................. 510/393 |
| 3,873,696 | 3/1975 | Randeri et al. ......................... 424/153 |
| 3,910,296 | 10/1975 | Karageozian et al. ..................... 134/2 |
| 3,931,319 | 1/1976 | Green et al. ........................... 564/286 |
| 4,026,945 | 5/1977 | Green et al. ........................... 526/294 |
| 4,407,791 | 10/1983 | Stark .................................. 424/80 |
| 4,414,127 | 11/1983 | Fu .................................... 252/95 |
| 4,438,011 | 3/1984 | Howes ................................. 252/106 |
| 4,462,922 | 7/1984 | Boskamp ............................ 252/174.12 |
| 4,497,897 | 2/1985 | Eilertsen et al. ....................... 510/530 |
| 4,519,934 | 5/1985 | Eilertsen et al. ....................... 510/530 |
| 4,525,346 | 6/1985 | Stark .................................. 424/80 |
| 4,537,706 | 8/1985 | Severson, Jr. ........................ 252/545 |
| 4,543,333 | 9/1985 | Eilersten et al. ....................... 435/188 |
| 4,614,549 | 9/1986 | Ogunbiyi et al. ........................ 134/19 |
| 4,615,882 | 10/1986 | Stockel ................................ 424/80 |
| 4,652,394 | 3/1987 | Inamorato et al. ...................... 510/321 |
| 4,758,595 | 7/1988 | Ogunbiyi et al. ...................... 514/635 |
| 4,786,436 | 11/1988 | Ogunbiyi et al. ...................... 252/352 |
| 4,836,986 | 6/1989 | Ogunbiyi et al. ........................ 422/28 |
| 5,089,163 | 2/1992 | Aronson et al. ....................... 252/135 |
| 5,096,607 | 3/1992 | Mowrey-McKee et al. .............. 422/28 |
| 5,145,644 | 9/1992 | Park et al. ............................ 422/28 |
| 5,270,002 | 12/1993 | Neff, II et al. .......................... 422/30 |
| 5,281,277 | 1/1994 | Nakagawa et al. ...................... 134/18 |
| 5,314,823 | 5/1994 | Nakagawa ............................ 435/264 |
| 5,356,555 | 10/1994 | Huth et al. ............................ 422/28 |
| 5,370,744 | 12/1994 | Chowhan et al. ....................... 134/42 |
| 5,409,546 | 4/1995 | Nakagawa et al. ..................... 134/42 |
| 5,439,817 | 8/1995 | Shetty et al. ......................... 435/222 |
| 5,460,658 | 10/1995 | Nakagawa et al. ..................... 134/42 |

FOREIGN PATENT DOCUMENTS

| | | |
|---|---|---|
| 1 092 036 | 12/1980 | Canada . |
| 1 150 907 | 8/1983 | Canada . |
| 0 456 467 | 5/1991 | European Pat. Off. . |
| 30 07 397 | 9/1981 | Germany . |
| 57-24526 | 5/1982 | Japan . |
| 89-180515 | 7/1989 | Japan . |
| 92-93919 | 3/1992 | Japan . |
| 92-143718 | 5/1992 | Japan . |
| 92-243215 | 8/1992 | Japan . |
| 92-370197 | 12/1992 | Japan . |
| 2 079 305 | 2/1984 | United Kingdom . |

OTHER PUBLICATIONS

Lo, J.; Silverman, H.; and Korb, D.; "Studies on cleaning solutions for contact lenses", *Journal of the American Optometric Association*, vol. 40, pp. 1106–1109 (1969).

*United States Pharmacopeia*, pp. 1149–1151 (1995).

Research Disclosure No. 35336, "Stabilization of liquid enzyme preparations for contact lens rinse" (Sep. 1993).

*Primary Examiner*—Richard L. Raymond
*Assistant Examiner*—Brenda Coleman
*Attorney, Agent, or Firm*—Gregg C. Brown; Michael C. Mayo

[57] ABSTRACT

Stable liquid enzyme compositions containing an ophthalmically acceptable enzyme and methods involving the combined use of these compositions with a polymeric antimicrobial agent are disclosed for the simultaneous cleaning and disinfecting of contact lens. Methods for a daily use regimen are also disclosed.

42 Claims, 3 Drawing Sheets

STABLE LIQUID ENZYME COMPOSITIONS AND METHODS OF USE IN CONTACT LENS CLEANING AND DISINFECTING SYSTEMS

The present application is a continuation of U.S. patent application Ser. No. 08/687334, filed Aug. 2, 1996, which is a continuation-in-part of U.S. patent application Ser. No. 08/544753, now U.S. Pat. No. 5,723,421, filed Oct. 18, 1995, which is a continuation-in-part of U.S. patent application Ser. No. 08/477001, now U.S. Pat. No. 5,604,190, filed on Jun. 7, 1995.

BACKGROUND OF THE INVENTION

The present invention relates to the field of contact lens cleaning and disinfecting. In particular, this invention relates to liquid enzyme compositions and methods for cleaning human-worn contact lenses with those compositions. The invention also relates to methods of simultaneously cleaning and disinfecting contact lenses by combining the liquid enzyme compositions of the present invention with a chemical disinfecting agent.

Various compositions and methods for cleaning contact lenses have been described in the patent and scientific literature. Some of these methods have employed compositions containing surfactants or enzymes to facilitate the cleaning of lenses. The first discussion of the use of proteolytic enzymes to clean contact lenses was in an article by Lo, et al. in the *Journal of The American Optometric Association*, volume 40, pages 1106–1109 (1969). Methods of removing protein deposits from contact lenses by means of proteolytic enzymes have been described in many publications since the initial article by Lo, et al., including U.S. Pat. No. 3,910,296 (Karageozian, et al.).

Numerous compositions and methods for disinfecting contact lenses have also been described. Those methods may be generally characterized as involving the use of heat and/or chemical agents. Representative chemical agents for this purpose include organic antimicrobials such as benzalkonium chloride and chlorhexidine, and inorganic antimicrobials such as hydrogen peroxide and peroxide-generating compounds. U.S. Pat. Nos. 4,407,791 and 4,525,346 (Stark) describe the use of polymeric quaternary ammonium compounds to disinfect contact lenses and to preserve contact lens care products. U.S. Pat. Nos. 4,758,595 and 4,836,986 (Ogunbiyi) describe the use of polymeric biguanides for the same purpose.

Various methods for cleaning and disinfecting contact lenses at the same time have been proposed. Methods involving the combined use of proteolytic enzymes and peroxides to clean and disinfect contact lenses simultaneously, are described in U.S. Pat. No. Re 32,672 (Huth, et al.). A representative method of simultaneously cleaning and disinfecting contact lenses involving the use of proteolytic enzymes and quaternary ammonium compounds is described in Japanese Patent Publication 57-24526 (Boghosian, et al.). The combined use of a biguanide (i.e., chlorhexidine) and liquid enzyme compositions to simultaneously clean and disinfect contact lenses is described in Canadian Patent No. 1,150,907 (Ludwig, et al.). Methods involving the combined use of dissolved proteolytic enzymes to clean and heat to disinfect are described in U.S. Pat. No. 4,614,549 (Ogunbiyi). The combined use of proteolytic enzymes and polymeric biguanides or polymeric quaternary ammonium compounds is described in copending, commonly assigned U.S. patent application Ser. No. 08/156,043 and in corresponding European Patent Application Publication No. 0 456 467 A2 (Rosenthal, et al.), as well as in U.S. Pat. No. 5,096,607 (Mowrey-McKee, et al.).

The commercial viability of most prior enzymatic cleaning products has depended on the use of stable enzyme tablets. More specifically, the use of solid enzymatic cleaning compositions has been necessary to ensure stability of the enzymes prior to use. In order to use such compositions, a separate packet containing a tablet must be opened, the tablet must be placed in a separate vial containing a solution, and the tablet must be dissolved in order to release the enzyme into the solution. This practice is usually performed only once a week due to the cumbersome and tedious procedure and potential for irritation and toxicity. Moreover, the enzymatic cleaning tablets contain a large amount of excipients, such as effervescent agents (e.g., bicarbonate) and bulking agents (e.g., sodium chloride). As explained below, such excipients can adversely affect both cleaning and disinfection of the contact lenses.

There have been prior attempts to use liquid enzyme compositions to clean contact lenses. However, those attempts have been hampered by the fact that aqueous liquid enzyme compositions are inherently unstable. When a proteolytic enzyme is placed in an aqueous solution for an extended period (i.e., several months or more), the enzyme may lose all or a substantial portion of its proteolytic activity. Steps can be taken to stabilize the compositions, but the use of stabilizing agents may have an adverse effect on the activity of the enzyme. For example, stabilizing agents can protect enzymes from chemical instability problems during storage in an aqueous liquid, by placing the enzymes in a dormant physical conformation. This conformation is referred to herein as being "partially denatured." However, such agents may also inhibit the ability of the enzymes to become active again (i.e., become "renatured") at the time of use. Finally, in addition to the general problems referred to above, a commercially viable liquid enzyme preparation for treating contact lenses must be relatively nontoxic, and must be compatible with other chemical agents used in treating contact lenses, particularly antimicrobial agents utilized to disinfect the lenses.

The following patents may be referred to for further background concerning prior attempts to stabilize liquid enzyme formulations: U.S. Pat. Nos. 4,462,922 (Boskamp); 4,537,706 (Severson); and 5,089,163 (Aronson). These patents describe detergent compositions containing enzymes. The detergent compositions may be used to treat laundry, as well as other industrial uses. Such detergents are not appropriate for treating contact lenses. The compositions of the present invention do not contain a detergent, or other agents potentially damaging or irritating to the eye.

U.S. Pat. No. 5,281,277 (Nakagawa) and Japanese Kokai Patent Applications Nos. 92-370197; 92-143718; and 92-243215 describe liquid enzyme compositions for treating contact lenses. The compositions of the present invention are believed to provide significant improvements relative to the compositions described in those publications.

SUMMARY OF THE INVENTION

The liquid enzyme compositions of the present invention contain critical amounts of selected stabilizing agents. The stabilizing agents utilized are combinations of a borate or boric acid compound and one or more 2-3 carbon polyols. The amounts of stabilizing agents utilized have been delicately balanced, such that maximum stability is achieved, while maximum activity is later obtained when the composition is put into use. Furthermore, the borate or boric acid compound also preserves the liquid enzyme compositions of the present invention from microbial contamination when the compositions are packaged in multiple use containers.

The present invention also provides methods for cleaning contact lenses with the above-described liquid enzyme compositions. In order to clean a soiled lens, the lens is placed in a few milliliters of an aqueous solution and a small amount, generally one to two drops, of the enzyme composition is added to the solution. The lens is then soaked in the resultant cleaning solution for a time sufficient to clean the lens.

The liquid enzyme compositions of the present invention are preferably combined with an aqueous disinfecting solution to simultaneously clean and disinfect contact lenses. As will be appreciated by those skilled in the art, the disinfecting solution must be formulated so as to be compatible with contact lenses. The antimicrobial activity of many chemical disinfecting agents is adversely affected by ionic solutes (e.g., sodium chloride). As explained below, the liquid enzyme compositions of the present invention are substantially nonionic, and therefore do not adversely affect the antimicrobial activity of such disinfecting agents. This is considered to be a major advantage of the present invention.

The enzyme compositions of the present invention are formulated as concentrated, multi-dose liquids, and consequently do not contain conventional enzyme tablet excipients, such as sodium chloride (bulking agent) and bicarbonate (effervescent agent). The liquid enzyme compositions of the present invention utilize an aqueous vehicle. The primary components of the vehicle are one or more polyols and water. Both of these components are non-ionic. The liquid enzyme compositions of the present invention are thus substantially nonionic, and therefore have very little impact on the ionic strength of a disinfecting solution, and little to no effect on the antimicrobial activity of disinfecting solutions.

The compositions and methods of the present invention provide greater ease of use. This ease of use enables contact lens users to clean their lenses 2 to 3 times a week, or more preferably, every day. It has been found that daily use of the liquid enzyme compositions of the present invention results in dramatically better cleaning and safety, as compared to the once-a-week enzyme cleaning regimens currently being utilized.

DETAILED DESCRIPTION OF THE INVENTION

It has been found that the use of a polyol in combination with a borate or boric acid compound achieves the stability and sustainable activity required in the liquid enzyme compositions of the present invention. While Applicants do not wish to be bound by any theory, it is believed that the stability of the enzymes utilized in the present invention is enhanced by partially denaturing the proteins. The enzymes are partially denatured by forming a complex with the stabilizing agents. The enzymes are denatured to a point where the enzymes are inactivated, but where renaturation is easily achieved by dilution of the denatured enzyme/stabilizing agent complex in an aqueous medium. It is believed that the stabilizing agents compete with water for hydrogen bonding sites on the proteins. Thus, a certain percentage of these agents will effectively displace a certain percentage of water molecules. As a result, the proteins will change conformation (partially denature) to an inactive and complexed (with the stabilizing agents) form. When the enzyme is in an inactive form, it is prevented from self-degradation and other spontaneous, chemically irreversible events. On the other hand, displacement of too many water molecules results in protein conformational changes that are irreversible. In order to obtain a stable liquid enzyme composition of significant shelf life and thus commercial viability, a delicate balance point of maximum stability and maximum reversible renaturation must be ascertained. Such a point has now been discovered.

The polyols utilized in the present invention are 2-3 carbon polyols. As used herein, the term "2-3 carbon polyol" refers to a compound with 2 to 3 carbon atoms and at least two hydroxy groups. Examples of 2-3 carbon polyols are glycerol, 1,2-propane diol ("propylene glycol"), 1,3-propane diol and ethylene glycol. Propylene glycol is the preferred 2-3 carbon polyol.

The borate or boric acid compounds which may be utilized in the present invention include alkali metal salts of borate, boric acid and borax. The most preferred borate or boric acid compound is sodium borate. As mentioned above, the borate or boric acid compound also contributes to the antimicrobial preservation of the liquid enzyme compositions of the present invention to a level effective for multi-use dispensing.

It has been found that certain amounts of a 2-3 carbon polyol and a borate or boric acid compound are critical for obtaining the stability and sustainable activity required in the liquid enzyme compositions of the present invention. It has been discovered that the combination of 50–70% volume/volume ("% v/v") of a 2-3 carbon polyol and 4–8% weight/volume ("% w/v") of a borate or boric acid compound is required to achieve the necessary criteria for efficacious and commercially viable liquid enzyme compositions, as described above. The combination of about 50% v/v of a 2-3 carbon polyol and about 7.6% w/v of sodium borate is most preferred. Examples 1, 2 and 3 below further illustrate appropriate and inappropriate concentrations of these stabilizing agents.

The enzymes which may be utilized in the compositions and methods of the present invention include all enzymes which: (1) are useful in removing deposits from contact lenses; (2) cause, at most, only minor ocular irritation in the event a small amount of enzyme contacts the eye as a result of inadequate rinsing of a contact lens; (3) are relatively chemically stable and effective in the presence of the anti-microbial agents described below; and (4) do not adversely affect the physical or chemical properties of the lens being treated. The proteolytic enzymes used herein must have at least a partial capability to hydrolyze peptide-amide bonds in order to reduce the proteinaceous material found in lens deposits to smaller water-soluble subunits. Typically, such enzymes will exhibit some lipolytic, amylolytic or related activities associated with the proteolytic activity and may be neutral, acidic or alkaline. In addition, separate lipases or carbohydrases may be used in combination with the proteolytic enzymes. For purposes of the present specification, enzymes which satisfy the foregoing requirements are referred to as being "ophthalmically acceptable."

Examples of ophthalmically acceptable proteolytic enzymes which may be utilized in the present invention include but are not limited to pancreatin, trypsin, subtilisin, collagenase, keratinase, carboxypeptidase, papain, bromelain, aminopeptidase, elastase, Aspergillo peptidase, pronase E (from *S. griseus*), dispase (from *Bacillus polymyxa*) and mixtures thereof. If papain is used, a reducing agent, such as N-acetylcysteine, may be required.

Microbially derived enzymes, such as those derived from Bacillus, Streptomyces, and Aspergillus microorganisms, represent a preferred type of enzyme which may be utilized in the present invention. Of this sub-group of enzymes, the most preferred are the Bacillus derived alkaline proteases generically called "subtilisin" enzymes.

The identification, separation and purification of enzymes is known in the art. Many identification and isolation techniques exist in the general scientific literature for the isolation of enzymes, including those enzymes having proteolytic and mixed proteolytic/lipolytic/amylolytic activity. The enzymes contemplated by this invention can be readily obtained by known techniques from plant, animal or microbial sources.

With the advent of recombinant DNA techniques, it is anticipated that new sources and types of stable proteolytic enzymes will become available. Such enzymes should be considered to fall within the scope of this invention so long as they meet the criteria set forth herein.

Pancreatin and subtilisin are preferred enzymes, and trypsin is the most preferred enzyme for use in the present invention. Pancreatin is extracted from mammalian pancreas, and is commercially available from various sources, including Scientific Protein Laboratories (Waunakee, Wis., U.S.A.), Novo Industries (Bagsvaerd, Denmark), Sigma Chemical Co. (St. Louis, Mo., U.S.A.), and Boehringer Mannheim (Indianapolis, Ind., U.S.A.). Pancreatin USP is a mixture of proteases, lipases and amylases, and is defined by the United States Pharmacopeia ("USP"). The most preferred form of pancreatin is Pancreatin 9X. As utilized herein, the term "Pancreatin 9X" means a filtered (0.2 microns) pancreatin containing nine times the USP protease unit content. Subtilisin is derived from Bacillus bacteria and is commercially available from various commercial sources including Novo Industries (Bagsvaerd, Denmark), Fluka Biochemika (Buchs, Switzerland) and Boehringer Mannheim (Indianapolis, Ind., U.S.A.). Trypsin is purified from various animal sources and is commercially available from Sigma Chemical Co. and Boehringer Mannheim.

The liquid enzyme compositions of the present invention will have an enzyme concentration sufficient to provide an effective amount of enzyme to remove substantially or to reduce significantly deposits of proteins, lipids, mucopolysaccharides and other materials typically found on human-worn contact lenses when a small amount of a composition is added to a diluent. As used herein, such a concentration is referred to as "an amount effective to clean the lens." The amount of enzyme used in the liquid enzyme compositions of the present invention will generally range from about 0.05 to 5% w/v. The selection of a specific concentration will depend on various factors, such as: the enzyme or combination of enzymes selected; the purity, specificity and efficacy of the enzyme(s) selected; the type of lenses to be cleaned; the intended frequency of cleaning (e.g., daily or weekly); and the intended duration of each cleaning.

During storage, some of the activity of the enzyme may be lost, depending on length of storage and temperature conditions. Thus, the liquid enzyme compositions of the present invention may be prepared with initial amounts of enzyme that exceed the concentration ranges described herein. The preferred compositions of the present invention will generally contain one or more enzymes in an amount of about 300–6000 PAU/mL. The compositions will most preferably contain about 900–2200 PAU/mL, which corresponds to pancreatin in the range of about 1 to 2% w/v; subtilisin in a range of about 0.1 to 0.3% w/v; and trypsin in the range of about 0.1 to 0.3% w/v. For purposes of this specification, a "proteolytic activity unit" or "PAU" is defined as the amount of enzyme activity necessary to generate one microgram (mcg) of tyrosine per minute ("mcg Tyr/min"), as determined by the casein-digestion, colorimetric assay described below.

Casein-digestion assay

A 5.0 mL portion of casein substrate (0.65% casein w/v) is equilibrated for 10 minutes (min) ±5 seconds (sec) at 37° C. A 1.0 mL portion of enzyme solution (0.2 mg/ml) is then added to the casein substrate and the mixture vortexed, then incubated for 10 min ±5 sec at 37° C. After incubation, 5.0 mL of 14% trichloroacetic acid is added and the resultant mixture immediately vortexed. The mixture is incubated for at least another 30 min, then vortexed and centrifuged for 15–20 min (approx. 2000 rpm). The supernatant of the centrifuged sample is filtered into a serum filter sampler and a 2.0 mL aliquot removed. To the 2.0 mL sample is added 5.0 mL of 5.3% $Na_2CO_3$. The sample is vortexed, 1.0 mL of 0.67 N Folin's Phenol reagent is added, and the sample is immediately vortexed again, then incubated for 60 min at 37° C. The sample is then read on a visible light spectrophotometer at 660 nanometers (nm) versus purified water as the reference. The sample concentration is then determined by comparison to a tyrosine standard curve.

The cleaning obtained with the liquid enzyme compositions of the present invention is a function of the time. The soaking times utilized will generally vary from about 1 hour to overnight. However, if longer soaking periods (e.g., 24 hours) were to be employed, lower concentrations than those described above can be utilized.

The cleaning methods of the present invention involve the use of a small amount of the above-described liquid enzyme compositions to facilitate the removal of proteins and other deposits from contact lenses. The amount of enzyme composition utilized in particular embodiments of the present invention may vary, depending on various factors, such as the purity of the enzyme utilized, the proposed duration of exposure of lenses to the compositions, the nature of the lens care regimen (e.g., the frequency of lens disinfection and cleaning), the type of lens being treated, and the use of adjunctive cleaning agents (e.g., surfactants). However, the cleaning methods of the present invention will generally employ an amount of the above-described liquid enzyme compositions sufficient to provide a final enzyme concentration of about 5–75 PAU/mL of solution, following dispersion of the liquid enzyme compositions in a disinfecting solution or other aqueous solvent. A final concentration of about 5–25 PAU/mL is preferred.

As indicated above, the liquid enzyme compositions of the present invention contain relatively minor amounts of ionic solutes. More specifically, the compositions do not contain bulking agents, effervescent agents or other ionic solutes commonly contained in prior enzyme tablets. The present compositions do contain the ionic solutes of borate or boric acid compounds and hydrochloric acid and/or sodium hydroxide, but the concentration of these solutes in the present compositions is relatively low. The compositions are therefore substantially nonionic. Moreover, as a result of the fact that the compositions are formulated as concentrated, multi-dose liquids, only a small amount of the compositions, generally one or two drops, is required to clean a contact lens. The present compositions therefore have very little impact on the ionic strength of disinfecting solutions. As explained below, this feature of the present invention is particularly important when the liquid enzyme compositions are combined with disinfecting solutions which contain ionic antimicrobial agents, such as polyquaternium-1.

The antimicrobial activity of disinfecting agents, particularly polymeric quaternary ammonium compounds such as polyquaternium-1, is adversely affected by high concentrations of sodium chloride or other ionic solutes. More specifically, polymeric quaternary ammonium compounds, and particularly those of Formula (I), below, lose antimicrobial activity when the concentration of ionic solutes in the disinfecting solution is increased. The use of solutions having low ionic strengths (i.e., low concentrations of ionic solutes such as sodium chloride) is therefore preferred. Since both ionic solutes (e.g., sodium chloride) and nonionic solutes (e.g., glycerol) affect the osmolality and tonicity of a solution, osmolality and tonicity are indirect measures of ionic strength. However, the low ionic strengths preferably utilized in the cleaning and disinfecting methods of the present invention generally correspond to tonicities/osmolalities in the range of hypotonic to isotonic, and more preferably in the range of 150 to 350 milliOsmoles per kilogram (mOs/kg). A range of 200 to 300 mOs/kg is particularly preferred, and an osmolality of about 220 mOs/kg is most preferred.

The liquid enzyme compositions of the present invention demonstrate effective cleaning efficacy while exhibiting minimal adverse effects or, more preferably, enhanced effects on the antimicrobial activity of disinfecting solutions. It has unexpectedly been discovered that the liquid enzyme compositions of the present invention enhance the antimicrobial activity of disinfecting solutions containing polyquaternium-1, a polymeric quaternary ammonium disinfecting agent. It has also been discovered that combinations of the liquid enzyme compositions and polyquaternium-1 disinfecting solutions become even more effective than the polyquaternium-1 disinfecting solutions alone when lenses are treated for extended periods of approximately one hour to overnight, with four to eight hours preferred. Since, for the sake of convenience, contact lenses are typically soaked overnight in order to be cleaned with enzymes or disinfected with chemical agents, this finding has practical significance. While Applicants do not wish to be bound by any theory, it is believed that the above-described enhancement of antimicrobial activity is due to the disruption or lysis of microbial membranes by the enzyme over time.

The cleaning methods of the present invention utilize an aqueous solvent. The aqueous solvent may contain various salts such as sodium chloride and potassium chloride, buffering agents such as boric acid and sodium borate, and other agents such as chelating agents and preservatives. An example of a suitable aqueous solvent is a saline solution, such as Unisol® Plus Solution (registered trademark of Alcon Laboratories).

The cleaning and disinfecting methods of the present invention utilize a disinfecting solution containing an antimicrobial agent. Antimicrobial agents can be oxidative, such as hydrogen peroxide, or non-oxidative polymeric antimicrobial agents which derive their antimicrobial activity through a chemical or physicochemical interaction with the organisms. As used in the present specification, the term "polymeric antimicrobial agent" refers to any nitrogen-containing polymer or co-polymer which has antimicrobial activity. Preferred polymeric antimicrobial agents include: polyquaternium-1, which is a polymeric quaternary ammonium compound; and polyhexamethylene biguanide ("PHMB") or polyaminopropyl biguanide ("PAPB"), which is a polymeric biguanide. These preferred antimicrobial agents are disclosed in U.S. Pat. Nos. 4,407,791 and 4,525,346, issued to Stark, and 4,758,595 and 4,836,986, issued to Ogunbiyi, respectively. The entire contents of the foregoing publications are hereby incorporated in the present specification by reference. Other antimicrobial agents suitable in the methods of the present invention include: other quaternary ammonium compounds, such as benzalkonium halides, and other biguanides, such as chlorhexidine. The antimicrobial agents used herein are preferably employed in the absence of mercury-containing compounds such as thimerosal.

The most preferred antimicrobial agents are polymeric quaternary ammonium compounds of the structure:

wherein:
R$_1$ and R$_2$ can be the same or different and are selected from:
N$^+$(CH$_2$CH$_2$OH)$_3$X$^-$,
N(CH$_3$)$_2$ or OH;
X$^-$ is a pharmaceutically acceptable anion, preferably chloride; and
n=integer from 1 to 50.

The most preferred compounds of this structure is polyquaternium-1, which is also known as Onamer M™ (registered trademark of Onyx Chemical Corporation) or as Polyquad® (registered trademark of Alcon Laboratories, Inc.). Polyquaternium-1 is a mixture of the above referenced compounds, wherein X$^-$ is chloride and R$_1$, R$_2$ and n are as defined above.

The above-described antimicrobial agents are utilized in the methods of the present invention in an amount effective to eliminate substantially or to reduce significantly the number of viable microorganisms found on contact lenses, in accordance with the requirements of governmental regulatory agencies, such as the United States Food and Drug Administration. For purposes of the present specification, that amount is referred to as being "an amount effective to disinfect" or "an antimicrobially effective amount." The amount of antimicrobial agent employed will vary, depending on factors such as the type of lens care regimen in which the method is being utilized. For example, the use of an efficacious daily cleaner in the lens care regimen may substantially reduce the amount of material deposited on the lenses, including microorganisms, and thereby lessen the amount of antimicrobial agent required to disinfect the lenses. The type of lens being treated (e.g., "hard" versus "soft" lenses) may also be a factor. In general, a concentration in the range of about 0.000001% to about 0.01% by weight of one or more of the above-described antimicrobial agents will be employed. The most preferred concentration of the polymeric quaternary ammonium compounds of Formula (I) is about 0.001% by weight.

Oxidative disinfecting agents may also be employed in the methods of the present invention. Such oxidative disinfecting agents include various peroxides which yield active oxygen in solution. Preferred methods will employ hydrogen peroxide in the range of 0.3 to 3.0% to disinfect the lens. Methods utilizing an oxidative disinfecting system are described in U.S. Pat. No. Re 32,672 (Huth, et al.), the entire contents of which are hereby incorporated in the present specification by reference.

As will be appreciated by those skilled in the art, the disinfecting solutions utilized in the present invention may contain various components in addition to the above-described antimicrobial agents, such as suitable buffering agents, chelating and/or sequestering agents and tonicity adjusting agents. The disinfecting solutions may also contain surfactants.

The methods of the present invention will typically involve adding a small amount of a liquid enzyme composition of the present invention to about 2 to 10 mL of an aqueous solvent or disinfecting solution, placing the soiled lens into the enzyme/solvent or enzyme/disinfectant solution, and soaking the lens for a period of time effective to clean or clean and disinfect the lens. The amount of liquid enzyme composition utilized can vary based on factors such as the amount of aqueous solvent or disinfecting solution used, but generally it is about 1 to 2 drops. Preferred methods involve adding 1 drop (approximately 30 μL) to 5 mL of aqueous solvent or disinfecting solution. The soiled lens can be placed in the aqueous solvent or disinfecting solution either before or after the addition of the liquid enzyme composition. Optionally, the contact lenses are first rubbed with a non-enzymatic daily surfactant cleaner prior to immersion in the enzyme/solvent or enzyme/disinfectant solution. The lens will typically be soaked overnight, but shorter or longer durations are contemplated by the methods of the present invention. A soaking time of 4 to 8 hours is preferred. The methods of the present invention allow the above-described regimen to be performed once per week, but more prefer ably, every day.

The following examples are presented to illustrate further, various aspects of the present invention, but are not intended to limit the scope of the invention in any respect.

EXAMPLE 1

A preferred liquid enzyme composition of the present invention, and a suitable disinfecting solution for use in combination with that composition, are described below:

A. Liquid Pancreatin Composition

The following liquid enzyme composition represents a preferred embodiment of the present invention:

| Ingredient | amount |
| --- | --- |
| Pancreatin (9X) | 2200 PAU/mL |
| Sodium borate | 7.62% (w/v) |
| Propylene glycol | 50% (v/v) |
| Water | QS |
| Hydrochloric acid/sodium hydroxide | QS** |

**corresponds to an amount to adjust the pH to 6.0
Note:
(w/v) means weight/volume;
(v/v) means volume/volume;
and QS means quantity sufficient.

The above formulation was prepared by first sequentially mixing propylene glycol, purified water, hydrochloric acid and sodium borate together. The solution was polish filtered (1.2 μm filter) into a sterile receiving tank, and then sterile filtered (0.2 μm filter). The required amount of pancreatin (about 1–2% w/v) was then dissolved in an appropriate amount of water and the solution was polish filtered (0.6 μm filter). This enzyme solution was then sterile filtered (0.2 μm filter) into the sterile receiving tank containing the sterilized propylene glycol/sodium borate solution. While mixing, the contents of the receiving tank were then brought to volume with an appropriate amount of water. The optimal pH of the above formulation is in the range of 6–7; a pH of 6 is most preferred.

Disinfecting Solution

The following formulation represents a preferred disinfecting solution:

| Ingredient | % (w/v) |
| --- | --- |
| Polyquaternium-1 | 0.001 + 10% excess |
| Sodium chloride | 0.48 |
| Disodium Edetate | 0.05 |
| Citric acid monohydrate | 0.021 |
| Sodium citrate dihydrate | 0.56 |
| Purified water | QS |

To prepare the above formulation, sodium citrate dihydrate, citric acid monohydrate, disodium edetate, sodium chloride and polyquaternium-1, in the relative concentrations indicated above, were mixed with purified water and the components allowed to dissolve by stirring with a mixer. Purified water was added to bring the solution to almost 100%. The pH was recorded at 6.3 and adjusted to 7.0 with NaOH. Purified water was added to bring the solution to 100%. The solution was stirred and a pH reading of 7.0 was taken. The solution was then filtered into sterile bottles and capped.

EXAMPLE 2

Preferred liquid subtilisin and liquid trypsin compositions of the present invention for use in combination with a suitable disinfecting solution, e.g. Example 1B., are described below:

| Ingredient | amount |
| --- | --- |
| I. Liquid Trypsin Composition | |
| Trypsin | 2200 PAU/mL |
| Sodium borate | 7.62% (w/v) |
| Propylene glycol | 50% (v/v) |
| Water | QS |
| Hydrochloric acid/sodium hydroxide | QS** |

**corresponds to an amount to adjust the pH to 6.0

| II. Liquid Subtilisin Composition | |
| --- | --- |
| Subtilisin | 900 PAU/mL |
| Sodium borate | 7.62% (w/v) |
| Propylene glycol | 50% (v/v) |
| Water | QS |
| Hydrochloric acid/sodium hydroxide | QS** |

**corresponds to an amount to adjust the pH to 6.0

The above liquid subtilisin and trypsin compositions are made in the same manner as the liquid pancreatin composition, described in Example 1.

EXAMPLE 3

A comparative study of the effects of varying amounts of borate and propylene glycol in liquid enzyme compositions was performed. Aliquots of the compositions were stored in a controlled temperature room (26.7°±2° C.). At 6 and 12 weeks, aliquots were assayed for enzyme activity by the casein-digestion method described above. Activity levels were compared with initial levels and expressed as percent remaining activity. Data demonstrating the criticality of the amounts of sodium borate and propylene glycol used in liquid enzyme compositions of the present invention versus alternative percentage amounts, as a function of enzyme stability, is given in Table I below:

TABLE I

COMPARISON OF THE STABILITY OF ALTERNATIVE LIQUID ENZYME COMPOSITIONS VERSUS A COMPOSITION OF THE PRESENT INVENTION

| Composition | 1 | 2 | 3 | 4 | 5 | 6 |
|---|---|---|---|---|---|---|
| Pancreatin 9X % (w/v) | 1.7 | 1.7 | 1.7 | 1.7 | 1.7 | 1.7 |
| Boric Acid % (w/v) | 0.155 | 0.155 | 0.155 | 0.155 | 0.155 | — |
| Sodium Borate % (w/v) | 0.035 | 0.035 | 0.035 | 0.035 | 0.035 | 7.62 |
| Purified Water (qs) | 60 | 50 | 40 | 30 | 10 | 50 |
| Propylene Glycol % (v/v) | 40 | 50 | 60 | 70 | 90 | 50 |
| Activity at 6 weeks (% of initial activity) | 71.9 | 86.6 | 88.2 | 92.9 | * | 97.7 |
| Activity at 12 weeks (% of initial activity) | 44 | 66 | 65 | 74 | * | 98.4 |

*Initial values showed low activity

Composition 6 illustrates a preferred embodiment of the present invention. Compositions 2, 3 and 4 contain propylene glycol in an amount required by the present invention, but do not contain an amount of borate (sodium borate and boric acid) required by the present invention. Compositions 1 and 5 contain amounts of propylene glycol and borate outside the ranges required by the present invention.

Activity measurements obtained for compositions 2–4, containing from 50–70% propylene glycol, showed that similar stability (86.6–92.9% at room temperature) was obtained after 6 weeks of incubation, while compositions 1 and 5, containing 40 or 90% propylene glycol, were significantly less stable (71.9% and an undetectable level, respectively). Compositions 1–5, were less stable (71.9–92.9%) than composition 6 (97.9%) through 6 weeks of incubation. Moreover, composition 6 exhibited a greater duration of stability, 98.4% at 12 weeks, as compared to a range of 44–74% for compositions 1–5.

EXAMPLE 4

Data demonstrating the stability of the liquid enzyme composition of Example 1 at temperatures of typical storage were ascertained. Aliquots of the composition were stored in a controlled temperature room (26.7°±2° C., RT), or in a chamber held to 35° C. At the appointed time, aliquots were tested for enzyme activity by the casein-digestion method described above. Activity levels were compared with initial levels and expressed as percent remaining activity. The results are presented in Table II below:

TABLE II

EFFECT OF STORAGE TIME ON A LIQUID PANCREATIN COMPOSITION AT ROOM TEMPERATURE (RT) AND AT 35° C.

| | % Remaining Activity | |
|---|---|---|
| Time (Weeks) | RT | 35° C. |
| 2 | 94.4 | 83.0 |
| 4 | 94.0 | 76.5 |
| 6 | 97.7 | 81.1 |
| 8 | 99.0 | 80.2 |
| 12 | 98.4 | 78.3 |

The data presented in Table II confirm the stability of liquid enzyme compositions of the present invention. The data are based on a compilation of 4 separate lots and experiments. The data show virtually no deleterious effect on enzyme activity through 12 weeks at room temperature, the final measurement being 98.4%. The liquid enzyme composition of Example 1 was also effective in maintaining activity at the elevated temperature of 35° C. for 12 weeks, showing approximately a 20% loss in activity.

EXAMPLE 5

It has been found that one of the protease components of pancreatin, trypsin, is significantly more stable than one of the other protease components, chymotrypsin. This finding was confirmed by a study which compared the relative stability of liquid enzyme compositions containing 0.3% w/v of trypsin and chymotrypsin, respectively. The compositions were identical to the composition described in Example 1 above, except for the enzyme component. Aliquots of the compositions were stored in a chamber maintained at 35° C. At the appointed time, aliquots were tested for enzyme activity by the azocasein digestion method described below. Activity levels were compared with initial levels and expressed as percent remaining activity. The results of the study are presented in Table III below.

Azocasein Method:

The following solutions are used in this assay:

1) Buffer solution: 0.05 M sodium phosphate buffer containing 0.9% sodium chloride, pH 7.6.
2) Substrate solution: 2 mg/ml azocasein in the buffer solution mentioned above.

The assay is initiated by mixing 1 ml of an appropriately diluted (such that the enzyme activity is in the range of standard curve) enzyme composition in phosphate buffer with 2 ml of azocasein substrate solution (2 mg/ml). After incubation at 37° C. for 20 minutes, the mixture is removed from the incubator and 1 ml of trichloroacetic acid (14% w/v) is added to stop the enzyme reaction. The mixture is vortexed well and allowed to stand at room temperature for 20 minutes. After centrifuging at 2500 rpm (with a Beckman GS-6R Centrifuge) for 15 minutes, the supernatant is filtered with a serum sampler. 2 ml of the clear yellow filtrate is then adjusted to a neutral pH with 0.4 ml of 0.1 N sodium hydroxide an d the absorbance of 440 nm wavelength light is measured with a spectrophotometer. The amount of azocasein hydrolyzed is calculated based on a standard curve of known concentrations of azocasein solution developed under identical conditions. An enzyme activity unit ("AZ U") is defined as that amount of enzyme which hydrolyzes 1 $\mu$g of azocasein substrate/minute at 37° C.

TABLE III

COMPARISON OF THE STABILITY OF LIQUID ENZYME
COMPOSITIONS CONTAINING TRYPSIN OR CHYMOTRYPSIN
STORED AT 35° C.

| | % Remaining Activity | |
|---|---|---|
| Time | Trypsin | Chymotrypsin |
| 24 hours | 100 | 79.8 |
| 1 week | 100 | 7.3 |
| 2 weeks | 96.0 | — |
| 3 weeks | 93.2 | * |
| 4 weeks | 93.2 | * |

*no measurements taken after 2 week time point, when all activity was lost

The trypsin composition demonstrated an excellent stability profile at 35° C., in contrast with the chymotrypsin composition, an alternative composition not part of the present invention. As such, liquid enzyme compositions containing trypsin alone, are the most preferred compositions of the present invention.

EXAMPLE 6

Data demonstrating the stability of the liquid trypsin composition of Example 2 at various temperatures was ascertained. Aliquots of the composition were stored at room temperature room ("RT"), or at 35°, 40° or 45° C. At the appointed time, aliquots were tested for enzyme activity by the azocasein method described above. Activity levels were compared with initial levels and expressed as percent remaining activity. The results are presented in Table IV below:

TABLE IV

STABILITY OF A LIQUID TRYPSIN COMPOSITION
STORED AT VARIOUS TEMPERATURES
% Activity Remaining

| | Temperature (° C.) | | | |
|---|---|---|---|---|
| Weeks | RT | 35 | 40 | 45 |
| 0 | 100.0 | 100.0 | 100.0 | 100.0 |
| 1 | 98.4 | 97.8 | 98.4 | 61.1 |
| 2 | 100.0 | 99.4 | 100.0 | 56.3 |
| 4 | 100.0 | 93.2 | 96.0 | 42.5 |
| 8 | 100.0 | 97.8 | 95.6 | |
| 12 | 100.0 | 95.9 | 93.8 | |

EXAMPLE 7

The disinfecting efficacy of the present invention was evaluated by determining the rate and extent of kill achieved with an aqueous system formed by combining the liquid enzyme composition and disinfecting solution described in Example 1 above. The system was tested against six microorganisms: *Staphylococcus epidermidis, Pseudomonas aeruginosa, Serratia marcescens, Candida albicans, Aspergillus fumigatus*, and *Herpes simplex*. The test procedures and results are described below.

For testing against *Staphylococcus epidermidis, Pseudomonas aeruginosa, Serratia marcescens, Candida albicans*, and *Aspergillus fumigatus* the following procedure was used:

A 0.1 mL volume of inoculum ($10^8$ colony forming units/mL) was first added to a 10 mL volume of the disinfecting solution of Example 1, followed by the addition of 2 drops of the liquid enzyme composition of Example 1. A similarly inoculated 10 mL volume of the disinfecting solution of Example 1 was used as a control. The solutions were maintained at room temperature throughout the test. Each microorganism and test solution was tested individually. Sets of four replicate (n=8) samples were tested for each organism.

At selected time intervals of 1, 2, 3, 4, 6, 8 and 24 hours, a 1 mL volume of the inoculated test solution containing *Staphylococcus epidermidis, Pseudomonas aeruginosa, Serratia marcescens, Candida albicans*, or *Aspergillus fumigatus* was removed and appropriate serial dilutions were made in sterile 0.9% sodium chloride solution dilution blanks. Pour-plates were prepared with soybean-casein digest agar containing 0.07% Asolectin and 0.5% Polysorbate 80. At Time 0, a 1.0 mL volume of the saline control was removed and serial dilution pour-plates were prepared using the same recovery medium and dilution blanks. The Time 0 saline control count was used as the initial count. The pour-plates were incubated at 30°–35° C. for appropriate incubation periods. The number of surviving organisms at each time interval was then determined. The results are summarized in Tables V–IX below.

For testing against *Herpes simplex* the following procedure was used:

5 mL of the disinfecting solution of Example 1 containing one drop of the liquid enzyme composition of Example 1, and a control solution containing 5 mL of the disinfecting solution, were inoculated with 125 microliters of *Herpes simplex* to yield a Tissue Culture Infective Dose-50 ($TCID_{50}$) of approximately $1 \times 10^5$. At time intervals of 1, 2, 3, 4, 6 and 8 hours, an aliquot of the test or control solution was removed and neutralized by mixing 1:1 with AOAC neutralizer (40 g Asolectin and 280 mL polysorbate 80 in 1 liter of 0.25 M phosphate buffer at pH 7.2) and diluting 10-fold in Minimum Essential Medium (MEM). One mL aliquots were plated into VERO monolayers, 4 replicates per dilution and allowed to absorb for 30 minutes at 37°±1° C. in 5±1% $CO_2$ in air. The sample from each time point was run in duplicate. The results are summarized in Table X below.

TABLE V

ANTIMICROBIAL ACTIVITY:
S. EPIDERMIDIS

| SAMPLE | TIME (HR) | LOG REDUCTION |
|---|---|---|
| Liquid pancreatin composition and disinfecting solution of Example 1 | 1 | 2.7 ± 0.2 |
| | 2 | 3.3 ± 0.1 |
| | 3 | 3.6 ± 0.2 |
| | 4 | 4.2 ± 0.2 |
| | 6 | 4.8 ± 0.2 |
| | 8 | 4.9 ± 0.1 |
| | 24 | 4.8 ± 0.1 |
| Control (disinfecting solution of Example 1) | 1 | 2.2 ± 0.1 |
| | 2 | 2.7 ± 0.1 |
| | 3 | 3.1 ± 0.1 |
| | 4 | 3.3 ± 0.1 |
| | 6 | 3.7 ± 0.1 |
| | 8 | 4.1 ± 0.3 |
| | 24 | 4.9 ± 0.1 |

TABLE VI

ANTIMICROBIAL ACTIVITY: P. AERUGINOSA

| SAMPLE | TIME (HR) | LOG REDUCTION |
|---|---|---|
| Liquid pancreatin | 1 | 2.2 ± 0.1 |
| composition and | 2 | 2.7 ± 0.1 |
| disinfecting solution of | 3 | 3.1 ± 0.2 |
| Example 1 | 4 | 3.1 ± 0.2 |
|  | 6 | 3.6 ± 0.1 |
|  | 8 | 3.9 ± 0.2 |
|  | 24 | 5.0 ± 0.2 |
| Control (disinfecting | 1 | 1.7 ± 0.1 |
| solution of Example 1) | 2 | 2.1 ± 0.1 |
|  | 3 | 2.4 ± 0.1 |
|  | 4 | 2.6 ± 0.1 |
|  | 6 | 3.1 ± 0.2 |
|  | 8 | 3.5 ± 0.1 |
|  | 24 | 4.8 ± 0.4 |

TABLE VII

ANTIMICROBIAL ACTIVITY: S. MARCESCENS

| SAMLE | TIME (HR) | LOG REDUCTION |
|---|---|---|
| Liquid pancreatin | 1 | 0.8 ± 0.1 |
| composition and | 2 | 1.2 ± 0.1 |
| disinfecting solution of | 3 | 1.5 ± 0.1 |
| Example 1 | 4 | 1.9 ± 0.0 |
|  | 6 | 2.6 ± 0.1 |
|  | 8 | 3.0 ± 0.1 |
|  | 24 | 4.8 ± 0.6 |
| Control (disinfecting | 1 | 0.1 ± 0.1 |
| solution of Example 1) | 2 | 0.4 ± 0.1 |
|  | 3 | 0.6 ± 0.1 |
|  | 4 | 0.9 ± 0.1 |
|  | 6 | 1.1 ± 0.1 |
|  | 8 | 1.4 ± 0.1 |
|  | 24 | 3.3 ± 0.1 |

TABLE VIII

ANTIMICROBIAL ACTIVITY: C. ALBICANS

| SAMPLE | TIME (HR) | LOG REDUCTION |
|---|---|---|
| Liquid pancreatin | 1 | 0.1 ± 0.1 |
| composition and | 2 | 0.1 ± 0.1 |
| disinfecting solution of | 3 | 0.1 ± 0.1 |
| Example 1 | 4 | 0.1 ± 0.0 |
|  | 6 | 0.1 ± 0.0 |
|  | 8 | 0.2 ± 0.1 |
|  | 24 | 0.2 ± 0.0 |
| Control (disinfecting | 1 | 0.1 ± 0.1 |
| solution of Example 1) | 2 | 0.0 ± 0.1 |
|  | 3 | 0.1 ± 0.0 |
|  | 4 | 0.1 ± 0.0 |
|  | 6 | 0.1 ± 0.0 |
|  | 8 | 0.1 ± 0.1 |
|  | 24 | 0.1 ± 0.1 |

TABLE IX

ANTIMICROBIAL ACTIVITY: A. FUMIGATUS

| SAMPLE | TIME (HR) | LOG REDUCTION |
|---|---|---|
| Liquid pancreatin | 1 | 0.1 ± 0.1 |
| composition and | 2 | 0.1 ± 0.0 |
| disinfecting solution of | 3 | 0.1 ± 0.0 |
| Example 1 | 4 | 0.2 ± 0.1 |
|  | 6 | 0.3 ± 0.1 |
|  | 8 | 0.3 ± 0.1 |
|  | 24 | 0.5 ± 0.1 |
| Control (disinfecting | 1 | 0.1 ± 0.1 |
| solution of Example 1) | 2 | 0.1 ± 0.1 |
|  | 3 | 0.1 ± 0.0 |
|  | 4 | 0.1 ± 0.1 |
|  | 6 | 0.2 ± 0.1 |
|  | 8 | 0.3 ± 0.1 |
|  | 24 | 0.5 ± 0.1 |

TABLE X

ANTIMICROBIAL ACTIVITY: HERPES SIMPLEX

| SAMPLE | TIME (HR) | LOG REDUCTION |
|---|---|---|
| Liquid pancreatin | 1 | 0.9 ± 0.7 |
| composition and | 2 | 0.7 ± 0.5 |
| disinfecting solution of | 3 | 1.4 ± 1.8 |
| Example 1 | 4 | 3.7 ± 0.4 |
|  | 6 | 3.7 ± 0.3 |
|  | 8 | 3.9 ± 0.1 |
| Control (disinfecting | 1 | 0.2 ± 0.2 |
| solution of Example 1) | 2 | 0.2 ± 0.3 |
|  | 3 | 0.2 ± 0.2 |
|  | 4 | 0.3 ± 0.2 |
|  | 6 | 0.2 ± 0.2 |
|  | 8 | 0.3 ± 0.4 |

As illustrated in Tables V–X, the log reductions achieved with the liquid enzyme/disinfecting solution combination were generally greater than the log reductions achieved with the disinfecting solution control. This difference was statistically significant for *S. epidermidis, P. aeruginosa, S. marcescens* and *H. simplex*. The antimicrobial activity against *C. albicans* and *A. fumagitus* was about equal.

EXAMPLE 8

The disinfecting efficacy of another embodiment of the present invention was evaluated by determining the rate and extent of kill achieved with an aqueous system formed by combining the subtilisin liquid enzyme composition of Example 2 and the disinfecting solution of Example 1. The system was tested against *Serratia marcescens*. The test procedure in Example 7 was followed. Sample times were 2, 4, 24 hours and 7 days, and log reductions were calculated for 4 and 24 hours. The test results, expressed as log reductions, are presented in Table XI below.

TABLE XI

EFFECTS OF A SUBTILISIN CONTAINING LIQUID ENZYME COMPOSITION ON THE ANTIMICROBIAL ACTIVITY OF A POLYQUATERNIUM-1 DISINFECTING SOLUTION

| | LOG REDUCTION | |
|---|---|---|
| Time | Disinfecting Solution Control | Liquid Enzyme (subtilisin) + Disinfecting Solution |
| 4 hours | 0.9 ± 0.1 | 1.3 ± 0.2 |
| 24 hours | 3.7 ± 0.4 | 3.4 ± 1.0 |

As illustrated in Table XI, the liquid enzyme composition containing subtilisin had an enhancing effect on the antimicrobial activity of the disinfecting solution of Example 1, at 4 hours.

EXAMPLE 9

The disinfecting efficacy of a further embodiment of the present invention was evaluated by determining the rate and extent of kill achieved with an aqueous system formed by combining the liquid trypsin composition of Example 2 and the disinfecting solution described in Example 1. The system was tested against *Serratia marcescens, Staphylococcus aureus, Pseudomonas aeruginosa, Candida albicans* and *Fusarium solani*. The test procedure in Example 7 was followed. Sample times were 4, 6 and 24 hours. The test results, expressed as log reductions are presented in Table XII below.

TABLE XII

EFFECTS OF A TRYPSIN CONTAINING LIQUID ENZYME COMPOSITION ON THE ANTIMICROBIAL ACTIVITY OF A POLYQUATERNIUM-1 DISINFECTING SOLUTION

| | | LOG REDUCTION | |
|---|---|---|---|
| Microorganism | Time (hours) | Liquid Trypsin Composition and disinfecting solution | Disinfecting solution alone |
| S. marcescens | 4 | 1.9 ± 0.1 | 1.3 ± 0.1 |
| | 6 | 2.0 ± 0.6 | 1.5 ± 0.1 |
| | 24 | 4.4 ± 0.8 | 3.4 ± 0.5 |
| S. aureus | 4 | 3.1 ± 0.2 | 2.6 ± 0.2 |
| | 6 | 3.5 ± 0.3 | 3.0 ± 0.0 |
| | 24 | 4.9 ± 0.0 | 4.6 ± 0.3 |
| P. aeruginosa | 4 | 3.8 ± 1.0 | 2.3 ± 0.9 |
| | 6 | 4.2 ± 0.7 | 2.9 ± 1.0 |
| | 24 | 4.9 ± 0.0 | 4.4 ± 0.5 |
| C. albicans | 4 | 0.1 ± 0.1 | 0.1 ± 0.2 |
| | 6 | 0.1 ± 0.2 | 0.1 ± 0.2 |
| | 24 | 0.1 ± 0.2 | 0.2 ± 0.3 |
| F. solani | 4 | 3.8 ± 0.6 | 3.4 ± 1.3 |
| | 6 | 4.5 ± 0.4 | 3.6 ± 0.3 |
| | 24 | 4.6 ± 0.2 | 4.3 ± 0.5 |

EXAMPLE 10

The following comparative example demonstrates the effectiveness of the liquid enzyme compositions of the present invention with different disinfecting agents. The effect of the liquid enzyme compositions of the present invention, in particular the liquid enzyme composition of Example 1 (referred to below as "Liquid Enzyme" or "LE"), on the antimicrobial activity of a polyquaternium-1 multi-purpose solution (Example 1B formulation) and a polymeric biguanide multi-purpose solution (ReNu® Multi-Purpose Solution) was evaluated.

Two drops of Liquid Enzyme were added to 10 mL of either the polyquaternium-1 disinfecting solution or the polymeric biguanide disinfecting solution. The respective disinfecting solutions alone were also tested as controls. The protocol described in Example 7 was followed. Microbiological data, in the form of log reductions achieved against *Staphylococcus epidermidis, Pseudomonas aeruginosa, Serratia marcescens, Candida albicans*, and *Aspergillus fumigatus*, were ascertained at 4 hours. The results are presented in Table XIII below.

TABLE XIII

ANTIMICROBIAL ACTIVITY OF A POLYQUATERNIUM-1 MULTI-PURPOSE SOLUTION AND A POLYMERIC BIGUANIDE MULTI-PURPOSE SOLUTION WITH LIQUID ENZYME*

| Organism | poly-quaternium-1 multi-purpose solution + LE** | polyquaternium-1 multi-purpose solution | ReNu® polymeric biguanide multi-purpose solution + LE** | ReNu® polymeric biguanide multi-purpose solution |
|---|---|---|---|---|
| A. fumigatus | 0.2 | 0.1 | 0.1 | 0.2 |
| C. albicans | 0.1 | 0.1 | 0.2 | 1.3 |
| S. marcescens | 1.9 | 0.9 | 1.1 | 3.2 |
| P. aeruginosa | 3.1 | 2.6 | 3.3 | 4.0 |
| S. epidermidis | 4.2 | 3.3 | 1.8 | 2.3 |

*disinfection time is 4 hours
**LE = the liquid pancreatin composition of Example 1

The results demonstrate no deleterious effects of Liquid Enzyme on the polyquaternium-1 disinfecting solution, and an enhancement of the *S. marcescens, P. aeruginosa* and *S. epidermidis* kill after 4 hours. Conversely, the Liquid Enzyme composition had a negative effect on the antimicrobial activity of the polymeric biguanide disinfecting solution. These results illustrate the unexpected results obtained with a preferred method of the present invention, wherein a polyquatemium-1 disinfecting solution is combined with a liquid enzyme composition of the present invention.

EXAMPLE 11

A 135 day study comparing the efficacy of the compositions and methods of the present invention with other known compositions and methods was performed. Three different clinical observations were made: 1) frequency of Type III and Type IV lens deposits (Rudko grading system); 2) frequency and reasons for lens replacement; and 3) frequency of significant slit-lamp findings. "Type III" and "Type IV" lens deposits are considered as heavily deposited lenses. A "slit lamp finding" is defined as an abnormality observed on the cornea, by a clinician using an optometrist's slit-lamp apparatus.

Three different cleaning formulations and their associated methods were compared with a method of the present invention ("LE"): 1) "Historical control"—a data set comprised of 5 different studies wherein the lens was cleaned daily with a surfactant cleaner followed by an 8 hour soaking in a disinfecting solution combined with a once per week, 8 hour soaking of the lens in a disinfecting solution containing a dissolved pancreatin tablet; 2) "Protocol 1"—a protocol utilizing a polyquaternium-1 disinfecting solution containing citrate (Example 1B formulation) wherein the lens is rubbed daily for several seconds with this solution and then soaked 8 hours in this solution, combined with a once per week, 8 hour soaking of the lens in a polyquatemium-1 disinfecting solution (Example 1B formulation) containing a dissolved pancreatin tablet; 3) "Protocol 2"—a protocol utilizing a polymeric biguanide disinfecting solution containing a surfactant, wherein the lens is rubbed daily for several seconds, then soaked in this solution for 8 hours, combined with a once per week soaking of the lens in a polymeric biguanide disinfecting solution containing a surfactant and a dissolved subtilisin tablet for a minimum of 15 minutes, followed by removing the lens and placing it in a fresh polymeric biguanide solution containing a surfactant and soaking for 8 hours; and 4) "LE"—a method and composition of the present invention wherein the lens is rubbed daily with a surfactant cleaner, followed by an 8 hour soaking in 5 mL of a polyquaternium-1 solution (Example 1B formulation) and 1 drop of the liquid enzyme composition of Example 1 ("Liquid Enzyme"). Table XIV, below, provides a tabulated comparison of the compositions and protocols of this study.

TABLE XIV

COMPARISON OF CLEANING AND DISINFECTING COMPOSITIONS AND PROTOCOLS

| | HISTORICAL | PROTOCOL 1 | PROTOCOL 2 | LE |
|---|---|---|---|---|
| CLEANING | Daily, with a surfactant cleaner | Daily, with polyquaternium-1 solution | Daily, with ReNu ® polymeric biguanide solution | Daily, with a surfactant cleaner |
| DISINFECTING | Daily (8 hrs) with a disinfecting solution | Daily (8 hrs) with polyquaternium-1 solution | Daily (8 hrs) with ReNu ® polymeric biguanide solution | Daily (8 hrs) with polyquaternium-1 solution |
| ENZYMATIC CLEANER | Weekly (8 hrs) with a disinfecting solution containing a dissolved pancreatin tablet | Weekly (8 hrs) with polyquaternium-1 solution containing a dissolved pancreatin tablet, no separate disinfecting step | Weekly (min. of 15 minutes) with ReNu ® polymeric biguanide solution containing a dissolved subtilisin tablet, followed by disinfecting step | Daily (8 hrs) with a Polyquaternium-1 solution containing 1 drop of Liquid Enzyme |

Figure 1:
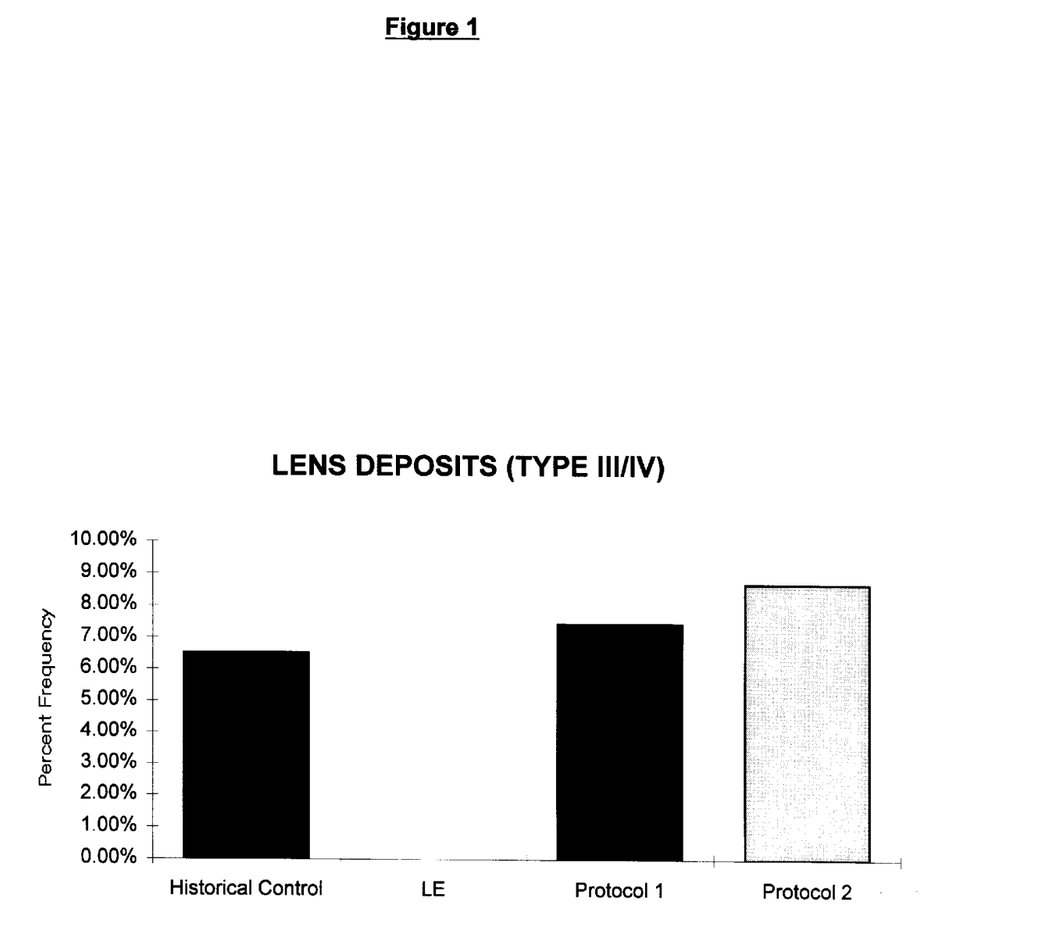
FIG. 1 is a histogram detailing the effects of a liquid enzyme composition of the present invention on Type III and Type IV lens deposits, when used daily during a 135 day clinical study.
Figure 2:
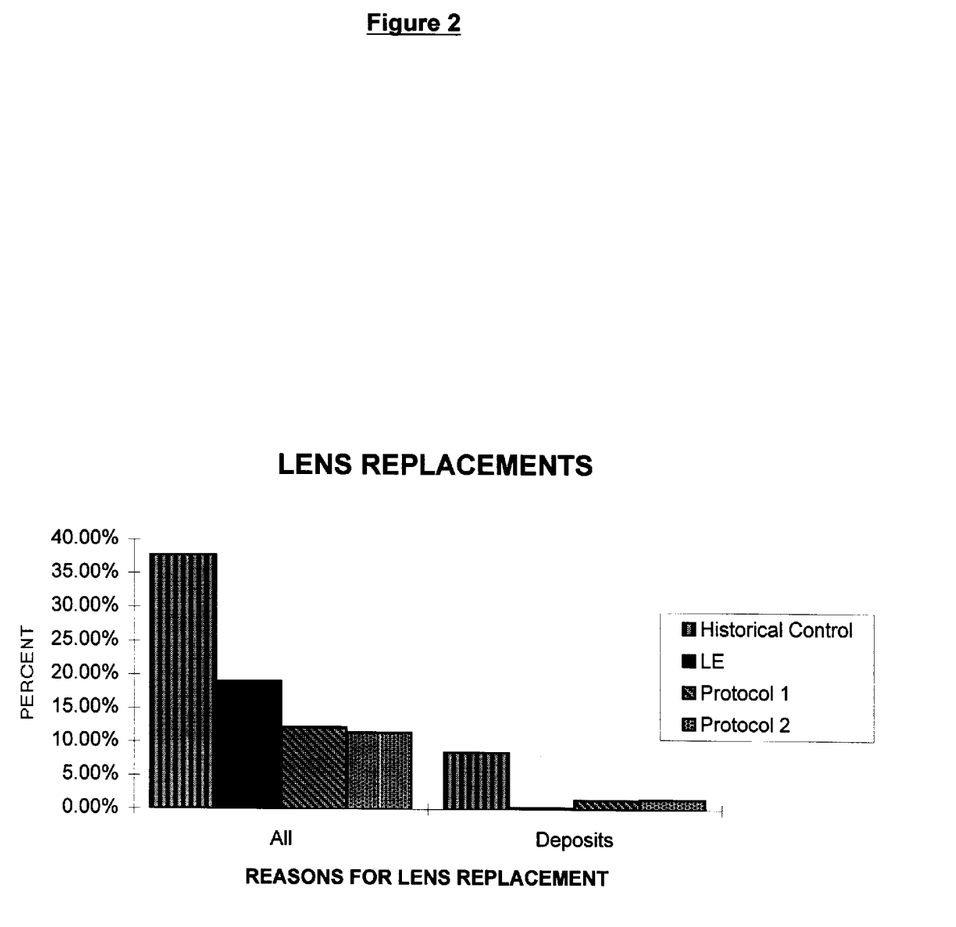
FIG. 2 illustrates the frequency and reasons for lens replacements during that study.
Figure 3:
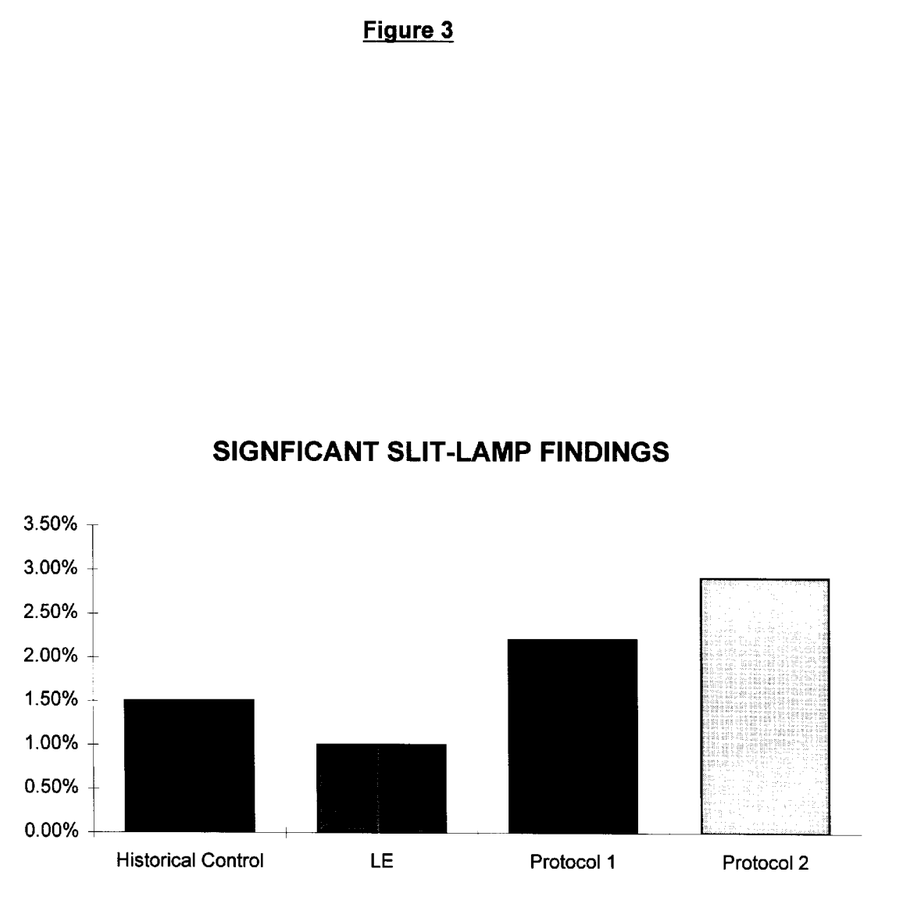
FIG. 3 illustrates the safety of the liquid enzyme compositions of the present invention relative to prior enzyme cleaner compositions, based on the incidence of significant slit-lamp findings during the clinical study.

The results are presented graphically in FIGS. 1–3. The protocol including the liquid enzyme composition of the present invention ("LE") demonstrated superior efficacy in maintaining lenses free of Type III and Type IV deposits, as compared to the other known methods and compositions. As shown in FIG. 1, the present invention eliminated Type III and Type IV lens deposits (0.0% frequency) while the other protocols exhibited a 6.5–8.4% lens deposit frequency.

FIG. 2 further demonstrates the cleaning efficacy of the compositions and methods of the present invention. Lenses cleaned with the LE composition needed replacement, due to lens deposits, on a frequency of 0.3% as compared to a range of 1.4–8.5% for the other compositions and methods studied. The LE composition also demonstrated lower slit-lamp findings as compared to the three other compositions and methods (FIG. 3).

The invention in its broader aspects is not limited to the specific details shown and described above. Departures may be made from such details within the scope of the accompanying claims without departing from the principles of the invention and without sacrificing its advantages.

What is claimed is:

1. A stable liquid enzyme composition for cleaning a contact lens comprising: an opthalmically acceptable proteolytic enzyme in an amount effective to clean the lens; a stabilizing system to maintain the proteolytic activity of said enzyme, said system consisting essentially of (i) 50–70% v/v of a 2-3 carbon polyol to stabilize the proteolytic enzyme in the liquid enzyme composition, and (ii) a borate compound selected from the group consisting of alkali metal salts of borate and boric acid, in an amount effective to enhance the stability of the proteolytic enzyme in the liquid enzyme composition; and water.

2. A composition according to claim 1, wherein the liquid enzyme composition contains the 2-3 carbon polyol and the borate compound in an amount effective to maintain the activity level of the proteolytic enzyme in the range of 300–6000 PAU per milliliter of the liquid enzyme composition, during storage of said composition.

3. A composition according to claim 2, wherein the proteolytic enzyme is selected from the group consisting of pancreatin, subtilisin and trypsin.

4. A composition according to claim 2, wherein the 2-3 carbon polyol is selected from the group consisting of: glycerol; 1,2-propane diol; 1,3-propane diol; and ethylene glycol.

5. A composition according to claim 2, wherein the proteolytic enzyme is selected from the group consisting of pancreatin, subtilisin and trypsin; the 2-3 carbon polyol is selected from the group consisting of glycerol, 1,2-propane diol, 1,3-propane diol and ethylene glycol; and the borate compound is selected from the group consisting of sodium borate and boric acid.

6. A composition according to claim 1, wherein the 2-3 carbon polyol comprises 1,2-propane diol.

7. A composition according to claim 6, wherein the proteolytic enzyme comprises pancreatin.

8. A composition according to claim 1, wherein the 2-3 carbon polyol comprises glycerol.

9. A composition according to claim 8, wherein the proteolytic enzyme comprises subtilisin.

10. A method for cleaning and disinfecting a contact lens which comprises:

forming an aqueous disinfectant/enzyme solution by dispersing a small amount of a liquid enzyme cleaning composition in an aqueous disinfecting solution containing an amount of an antimicrobial agent effective to disinfect the lens, said cleaning composition comprising; an ophthalmically acceptable proteolytic enzyme in an amount effective to clean the lens; a stabilizing system to maintain the proteolytic activity of said enzyme, said system consisting essentially of (i)

50–70% v/v of a 2-3 carbon polyol to stabilize the proteolytic enzyme in the cleaning composition, and (ii) a borate compound selected from the group consisting of alkali metal salts of borate and boric acid, in an amount effective to enhance the stability of the proteolytic enzyme in the cleaning composition; and water; and soaking the lens in the aqueous disinfectant/enzyme solution for a period of time sufficient to clean and disinfect the lens.

11. A method according to claim 10, wherein the liquid enzyme cleaning composition contains the 2-3 carbon polyol and the borate compound in an amount effective to maintain the activity level of said proteolytic enzyme in the range of 300–6000 PAU per milliliter of the liquid enzyme composition, during storage of said composition.

12. A method according to claim 11, wherein the proteolytic enzyme is selected from the group consisting of pancreatin, subtilisin and trypsin.

13. A method according to claim 11, wherein the 2-3 carbon polyol is selected from the group consisting of: glycerol, 1,2-propane diol, 1,3-propane diol, and ethylene glycol.

14. A method according to claim 11, wherein the proteolytic enzyme is selected from the group consisting of pancreatin, subtilisin and trypsin; the 2-3 carbon polyol is selected from the group consisting of glycerol, 1,2-propane diol, 1,3-propane diol and ethylene glycol; and the borate compound is selected from the group consisting of sodium borate and boric acid.

15. A method according to claim 10, wherein the antimicrobial agent comprises polyquaternium-1.

16. A method according to claim 15, wherein the 2-3 carbon polyol comprises 1,2-propane diol.

17. A method according to claim 16, wherein the proteolytic enzyme comprises pancreatin.

18. A method according to claim 10, wherein antimicrobial agent comprises polyhexamethylene biguanide.

19. A method according to claim 18, wherein the 2-3 carbon polyol comprises glycerol.

20. A method according to claim 19, wherein the proteolytic enzyme comprises subtilisin.

21. A method of cleaning a contact lens which comprises:
forming an aqueous enzymatic cleaning solution by dispersing a small amount of a liquid enzyme composition in an aqueous solvent, said liquid enzyme composition comprising: an ophthalmically acceptable proteolytic enzyme in an amount effective to clean the lens; a stabilizing system to maintain the proteolytic activity of said enzyme, said system consisting essentially of (i) 50–70% v/v of a 2-3 carbon polyol to stabilize the proteolytic enzyme in the liquid enzyme composition, and (ii) a borate compound selected from the group consisting of alkali metal salts of borate and boric acid, in an amount effective to enhance the stability of the proteolytic enzyme in the liquid enzyme composition; and water; and soaking the lens in the enzymatic cleaning solution for a period of time sufficient to clean the lens.

22. A method according to claim 21, wherein the liquid enzyme composition contains the 2-3 carbon polyol and the borate compound in an amount effective to maintain the activity level of the proteolytic enzyme in the range of 300–6000 PAU per milliliter of the liquid enzyme composition, during storage of said composition.

23. A method according to claim 22, wherein the proteolytic enzyme is selected from the group consisting of pancreatin, subtilisin and trypsin.

24. A method according to claim 22, wherein the 2-3 carbon polyol is selected from the group consisting of: glycerol; 1,2-propane diol; 1,3-propane diol; and ethylene glycol.

25. A method according to claim 22, wherein the proteolytic enzyme is selected from the group consisting of pancreatin, subtilisin and trypsin; the 2-3 carbon polyol is selected from the group consisting of: glycerol, 1,2-propane diol, 1,3-propane diol and ethylene glycol; and the borate compound is selected from the group consisting of sodium borate and boric acid.

26. A method according to claim 21, wherein the 2-3 carbon polyol comprises 1,2-propane diol.

27. A method according to claim 26, wherein the proteolytic enzyme comprises pancreatin.

28. A method according to claim 21, wherein the 2-3 carbon polyol comprises glycerol.

29. A method according to claim 28, wherein the proteolytic enzyme comprises subtilisin.

30. A liquid enzyme composition for removing protein deposits from contact lenses, comprising:
an ophthalmically acceptable proteolytic enzyme in an amount of 300 to 6,000 PAU per milliliter of the liquid enzyme composition;
a stabilizing system to maintain the proteolytic activity of said enzyme, said stabilizing system consisting essentially of (i) 50 to 70% v/v of a 2-3 carbon polyol to stabilize the enzyme in the liquid enzyme composition, and (ii) an amount of a borate compound effective to further enhance the stability of the enzyme in the liquid enzyme composition, said stabilizing system acting to maintain the concentration of the proteolytic enzyme in the range of 300 to 6,000 PAU per milliliter of the liquid enzyme composition, during storage of said composition; and water.

31. A liquid enzyme composition according to claim 30, wherein the proteolytic enzyme is selected from the group consisting of pancreatin, subtilisin and trypsin, and the 2-3 carbon polyol is selected from the group consisting of: glycerol; 1,2-propane diol; 1,3-propane diol; and ethylene glycol.

32. A liquid enzyme composition according to claim 31, wherein the proteolytic enzyme comprises pancreatin and the 2-3 carbon polyol comprises 1,2-propane diol.

33. A liquid enzyme composition according to claim 31, wherein the proteolytic enzyme comprises subtilisin and the 2-3 carbon polyol comprises glycerol.

34. A method for cleaning and disinfecting a contact lens which comprises:
placing the lens in an aqueous disinfecting solution containing an amount of an antimicrobial agent effective to disinfect the lens;
forming an aqueous disinfectant/enzyme solution by dispersing a small amount of a liquid enzyme cleaning composition in the disinfecting solution, said liquid enzyme composition comprising: an ophthalmically acceptable proteolytic enzyme in an amount of 300 to 6,000 PAU per milliliter of the liquid enzyme composition; a stabilizing system to maintain the proteolytic activity of said enzyme, said stabilizing system consisting essentially of (i) 50 to 70% v/v of a 2-3 carbon polyol to stabilize the enzyme in the liquid enzyme composition, and ( an amount of a borate compound effective to further enhance the stability of the enzyme in the liquid enzyme composition, said stabilizing system acting to maintain the concentration of the proteolytic enzyme in the range of 300 to 6,000 PAU per milliliter of the liquid enzyme composition, during storage of said composition; and water; and soaking the lens in the aqueous disinfectant/enzyme solution for a period of time sufficient to clean and disinfect the lens.

35. A method according to claim 34, wherein the antimicrobial agent is selected from the group consisting of polyquaternium-1 and polyhexamethylene biguanide; the proteolytic enzyme is selected from the group consisting of pancreatin and subtilisin; and the 2-3 carbon polyol is selected from the group consisting of: glycerol; 1,2-propane diol; 1,3-propane diol; and ethylene glycol.

36. A method according to claim 35, wherein the antimicrobial agent comprises polyquaternium-1, the proteolytic enzyme comprises pancreatin, and the 2-3 carbon polyol comprises 1,2-propane diol.

37. A method according to claim 35, wherein the antimicrobial agent comprises polyhexamethylene biguanide, the proteolytic enzyme comprises subtilisin, and the 2-3 carbon polyol comprises glycerol.

38. A method for cleaning and disinfecting a contact lens which comprises:

forming an aqueous disinfectant/enzyme solution by dispersing a small amount of a liquid enzyme cleaning composition in an aqueous disinfecting solution containing 0.000001 to 0.01% of weight of polyquaternium-1, said liquid enzyme composition comprising: pancreatin in an amount of 300 to 6,000 PAU per milliliter of the liquid enzyme composition; a stabilizing system to maintain the proteolytic activity of the pancreatin , said stabilizing system consisting essentially of (i) 50 to 70% v/v of a 2-3 carbon polyol to stabilize the pancreatin in the liquid enzyme composition, and (ii) an amount of a borate compound effective to enhance the stability of the pancreatin in the liquid enzyme composition, said stabilizing system acting to maintain the activity of the pancreatin in the range of 300 to 6,000 PAU per milliliter of the liquid enzyme composition, during storage of said composition; and water; and soaking the lens in the aqueous disinfectant/enzyme solution for a period of time sufficient to clean and disinfect the lens.

39. A method according to claim 38, wherein the concentration of polyquaternium-1 in the disinfecting solution is 0.001% by weight.

40. A method according to claim 39, wherein the 2-3 carbon polyol comprises 1,2-propane diol.

41. A method of cleaning and disinfecting a contact lens, comprising:

forming an aqueous disinfectant/enzyme solution by dispersing a small amount of a liquid enzyme cleaning composition in an aqueous disinfecting solution containing 0.000001 to 0.01% by weight of polyhexamethylene biguanide, said cleaning composition comprising: subtilisin in an amount of 300 to 6,000 PAU per milliliter of the liquid enzyme composition; a stabilizing system to maintain the proteolytic activity of the subtilisin, said stabilizing system consisting essentially of (i) 50 to 70% v/v of a 2-3 carbon polyol to stabilize the subtilisin in the liquid enzyme composition, and (ii) an amount of a borate compound effective to enhance the stability of the subtilisin in the liquid enzyme composition, said stabilizing system acting to maintain the activity of the subtilisin in the range of 300 to 6,000 PAU per milliliter of the liquid enzyme composition, during storage of said composition; and water; and soaking the lens in the aqueous disinfectant/enzyme solution for a period of time sufficient to clean and disinfect the lens.

42. A method according to claim 41, wherein the 2-3 carbon polyol comprises glycerol.

* * * * *